United States Patent
Wardaszka

(10) Patent No.: US 10,021,954 B2
(45) Date of Patent: Jul. 17, 2018

(54) SLEEPING BEAUTY MASK

(71) Applicant: Sylvia Wardaszka, Yonkers, NY (US)

(72) Inventor: Sylvia Wardaszka, Yonkers, NY (US)

( * ) Notice: Subject to any disclaimer, the term of this patent is extended or adjusted under 35 U.S.C. 154(b) by 588 days.

(21) Appl. No.: 14/577,599

(22) Filed: Dec. 19, 2014

(65) Prior Publication Data

US 2015/0173487 A1    Jun. 25, 2015

Related U.S. Application Data

(60) Provisional application No. 61/918,150, filed on Dec. 19, 2013.

(51) Int. Cl.
*A61F 7/00* (2006.01)
*A45D 44/00* (2006.01)
*A61F 9/04* (2006.01)

(52) U.S. Cl.
CPC .............. *A45D 44/002* (2013.01); *A61F 9/04* (2013.01)

(58) Field of Classification Search
CPC ............ A45D 44/002; A61F 9/04; A61F 7/00
USPC ......................................................... 607/109
See application file for complete search history.

(56) References Cited

U.S. PATENT DOCUMENTS

| | | | |
|---|---|---|---|
| 4,872,217 A | 10/1989 | Kitayama | |
| 5,343,561 A | 9/1994 | Adamo | |
| D465,234 S | 11/2002 | Gordon | |
| D489,749 S | 5/2004 | Landvik | |
| 8,365,733 B2 | 2/2013 | Rutan | |
| 2003/0014096 A1* | 1/2003 | Burkhart | A61F 7/02 607/109 |
| 2010/0122398 A1 | 5/2010 | Noelle | |
| 2014/0288624 A1* | 9/2014 | Wasko | A61F 7/02 607/109 |
| 2014/0331383 A1* | 11/2014 | Bially | A61F 9/04 2/173 |

OTHER PUBLICATIONS

Merriam-Webster Definition of Cavity https://www.merriam-webster.com/dictionary/cavity.*

* cited by examiner

*Primary Examiner* — Leslie Deak
*Assistant Examiner* — Gabriella Burnette
(74) *Attorney, Agent, or Firm* — Global Intellectual Property Agency, LLC; Jordan Sworen

(57) ABSTRACT

The present invention is an improved sleeping mask that concurrently applies beauty products. The sleeping mask, in its preferred embodiment, includes an eye cover, adjustable strap, and internal pockets having applicator sponge pads therein. Any desired beauty care product can be placed on the applicator sponge pads. The device is worn like any conventional sleeping mask so that the internal pockets directly contact the user's skin. In this way, the beauty care product on the applicator sponge pads can be applied to the user's skin throughout the night. The pockets may be perforated to allow beauty care products to permeate therethrough and treat the skin.

8 Claims, 2 Drawing Sheets

SLEEPING BEAUTY MASK

CROSS REFERENCE TO RELATED APPLICATION

This application claims the benefit of U.S. Provisional Application No. 61/918,150 filed on Dec. 19, 2013. The above identified patent application is herein incorporated by reference in its entirety to provide continuity of disclosure.

BACKGROUND OF THE INVENTION

Field of the Invention

The present invention relates to a device for applying beauty care products overnight. More specifically, the present invention pertains to an improved sleeping mask that aids in the application of beauty treatment at night while sleeping. The sleeping beauty mask is designed to work like a conventional sleeping mask, but with the additional utility of effective and continuous nighttime application of beauty products.

Great skin is smooth, even-toned, and dewy. Healthy skin starts with a commitment to regular skin care regimen. To get those results, there needs to be an understanding of how products work together, how they benefit your skin, and the order of application most beneficial. For example, over time, skin gets dry because it becomes less effective at holding in moisture. Treatments that contain hydrating ingredients and humectants may rectify or mitigate some of those effects and create a plumper complexion. Or as a person ages, it becomes more difficult for skin to renew itself, which can make complexion appear reddish. The repair process can be sped up by using an exfoliating serum.

Bedtime is often the best time to apply skincare because cell turnover is faster and body temperature rises while sleeping. Therefore, creams and serums melt deeper into skin. Products like sleeping facial masks are loaded with moisturizers, antioxidants, and retinols that help skin appear softer and smoother by the morning.

However, overnight skin treatment can often be messy. Bed sheets and pillow covers may be ruined, or these items may have to be frequently washed as the overnight skin products have stained the bed sheets and pillow cases. Towels may be placed over the bed and pillows to minimize damage, but even so, these items still have to be washed every morning. Furthermore, towels can slide or shift throughout the night, rendering it ineffective to create a barrier against the bed sheets and pillow cases.

The present invention provides an overnight skin treatment application in a conventional sleeping mask. In the preferred embodiment, the present invention comprises a face portion, an adjustable strap, and internal pockets. The internal pockets are located so that it directly aligns with the user's forehead and cheeks when worn. Furthermore, the internal pockets comprise a defined volume that allows for applicator sponge pads to be inserted and held therein. In the preferred embodiment, the internal pockets are located on the interior surface of the sleeping beauty mask and positioned along the forehead, and left and right cheek. Any desired beauty care product, such as creams, serums or moisturizers, can be applied to the sponge pads.

The internal pockets contain a porous surface that permits skin care products to permeate through the pocket and onto the user's skin. In other embodiments, the internal pockets may comprise a slit so that a portion of the pads extends out of the pockets to directly contact the user's skin. The sponge pads may be reusable or disposable, depending upon embodiment.

Description of the Prior Art

Devices have been disclosed in the prior art that relate to sleeping masks and respiratory masks. These include devices that have been patented and published in patent application publications. One of these devices describes a sleeping mask that includes internal depressions to prevent the mask from making contact with the eyes. Another device discloses a respiratory mask that includes a liner to protect the skin of a user. These devices, however, do not disclose a sleeping beauty mask that includes internal pockets that are designed to hold sponge pads, wherein the sponge pads can be filled with a desired beauty care product. The foregoing is a list of devices deemed most relevant to the present disclosure, which are herein described for the purposes of highlighting and differentiating the unique aspects of the present invention, and further highlighting the drawbacks existing in the prior art.

Specifically, U.S. Pat. No. 4,872,217, to Kitayama and U.S. Design Pat. No. D489749 to Landvik disclose conventional sleeping masks. The Kitayama device relates to a conventional eye mask comprising a main member being formed by a plate and a long rib portion being formed along an inner edge portion of main member, whereby the long rib portion contacts a periphery of an eye. Due to the long rib portion, the main member does not directly contact the eyes. Similarly, Landvik discloses a mask with a portion for substantially covering the eyes, forehead and cheeks, and an adjustable strap attached thereto.

Unlike the present invention, however, the devices of Kitayama and Landvik are limited in that the foregoing devices can only function as a sleeping mask. The present invention comprises a beauty mask that can function as a sleeping mask while also serving as an applicator for beauty care products. The present invention includes internal pockets that are configured for holding sponge pads that can be saturated with various types of skin care products. Thus, a user can wear the mask while sleeping, whereby wearing the mask allows the user to apply skin care products to his or her skin.

Similarly, U.S. Published Patent Application Number 2010/0122398 to Luciano discloses a sleeping mask apparatus for protecting a wearer's eyelashes during sleep. The sleeping mask comprises a face portion configured to cover an area of the wearer's face generally bounded by the wearer's forehead, beneath the wearer's eyes, and across the wearer's nose bridges. The face portion also comprises an inner surface having a perimeter and a pair of relatively rigid side portions, wherein the side portions are substantially perpendicular to the face portion. In this way, only the perimeter portion contacts the wearer's face, thereby preventing the sleeping mask from contacting the wearer's eyelashes. The purpose and design of the Luciano device, however, differ from the present invention in that the present invention is not designed to prevent the underside of the sleeping mask from contacting the user's face. Rather, the present invention is designed to contact the user's skin in order to apply skin care products to the user's face when wearing the device.

Additionally, U.S. Pat. No. 5,343,561 to Adamo discloses a sleeping mask with an improved fastening function. The sleeping mask comprises side parts that extend into a region adjacent to a wearer's ear. Additionally, the sleeping mask comprises receiving pockets for the outer ears on the inner side facing the head. The receiving pockets also offer a cover for the outer ears resulting in sound muffling. Likewise, U.S. Design Pat. No. D465234 to Gordon discloses a conventional face mask that extends on the side to also cover the ears. Thus, Adamo and Gordon disclose face masks that serves as sound muffler and not for skin care treatment.

Finally, U.S. Pat. No. 8,365,733 to Rutan is a liner for use with a respiratory mask, such as a continuous positive airway pressure (CPAP) mask. The respiratory mask includes a body constructed from an absorbent material, wherein the body includes an outer edge, an inner edge, and an opening bounded by the inner edge. The Rutan device is directed toward a liner to protect the skin of a person using a respiratory mask. Thus, Rutan does not disclose a sleeping mask or an applicator for skin care products.

The devices disclosed in the prior art have several known drawbacks. Most of the prior art devices are limited as they function only a sleeping mask, while other devices disclose a sleeping mask that can reduce noise or protect the wearer's eyelashes. Accordingly, none of these devices disclose a sleeping mask that can function also as a device for beauty care application. The present invention overcomes these limitations by disclosing such a device that operates as a sleeping mask while also functioning as an applicator for skin care products, whereby the present invention is designed to contact the user's skin in order to apply skin care products to the user's face when wearing the device. More specifically, the present invention comprises a mask with internal pockets having sponge applicator pads that can apply beauty products to the user's skin.

It is therefore submitted that the present invention is substantially divergent in design elements from the prior art, and consequently it is clear that there is a need in the art for an improvement to sleeping masks and beauty care application. In this regard, the instant invention substantially fulfills these needs.

SUMMARY OF THE INVENTION

In view of the foregoing disadvantages inherent in the known types of sleeping masks now present in the prior art, the present invention provides a new and improved sleeping mask wherein the same can be utilized for applying skin care products overnight.

It is therefore an object of the invention to provide a new and improved sleeping mask that has all of the advantages of the prior art and none of the disadvantages.

Another object of the present invention is to provide a new and improved sleeping mask that can apply overnight skin care treatment while reducing mess and increasing convenience to the user.

An additional object of the present invention is to provide a new and improved sleeping mask that comprises a face portion, an adjustable strap, and internal pockets having applicator sponge pads therein.

Another object of the present invention is to provide a new and improved sleeping mask that is configured to cover an area of the user's face generally bounded by the user's forehead, temples, cheeks, and that extends across the nose bridge.

Another object of the present invention is to provide a new and improved sleeping mask that holds applicator sponge pads impregnated with various types of beauty products so as to allow the user to apply beauty care products throughout the night as the user is wearing the sleeping mask.

Still yet another object of the present invention is to provide a new and improved sleeping mask that is adapted to block out light so that it can be utilized as a sleeping mask.

Still yet another object of the present invention is to provide a new and improved sleeping mask wherein the device may be readily fabricated from materials that permit relative economy and are commensurate with durability.

Other objects, features, and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein the numeral annotations are provided throughout.

DETAILED DESCRIPTION OF THE INVENTION

Figure 1:
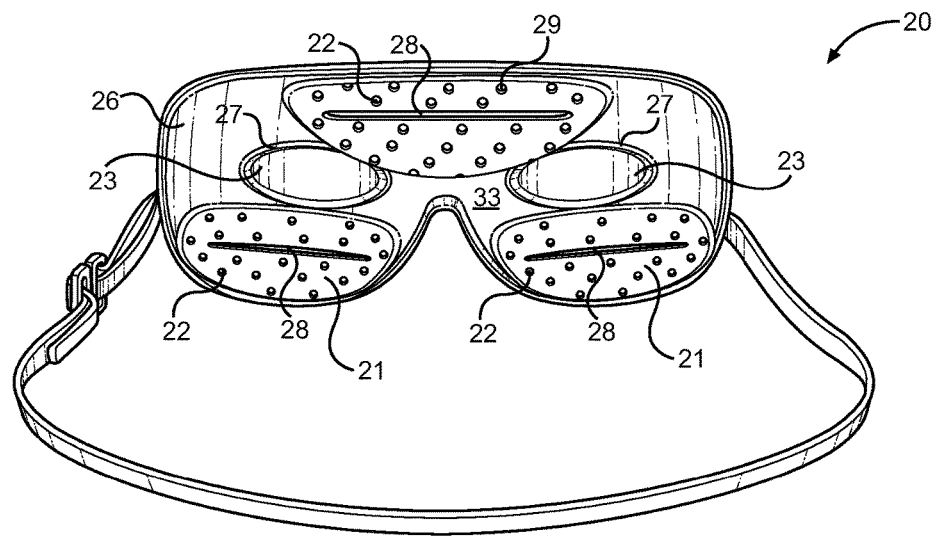
FIG. 1 shows a reverse view of the preferred embodiment of the present invention.

References are made herein to the attached drawings. Like reference numerals are used throughout the drawings to depict like or similar elements of the sleeping beauty mask. For the purposes of presenting a brief and clear description of the present invention, the preferred embodiment will be discussed as used to apply skin care products overnight, as well as block out light to promote sleep. The figures are intended for representative purposes only and should not be considered to be limiting in any respect.

Referring now to FIG. 1, there is shown a reverse view of the preferred embodiment of the sleeping beauty mask 20 of the present invention. In the illustrated embodiment, the sleeping beauty mask 20 is adapted to fit around a person's head to cover one's eyes, forehead, temples, and cheeks. The sleeping beauty mask 20 comprises an exterior surface that is coextensive with an interior surface 33, defining a face portion 26, eye cavities 23, internal pockets 21, 29, and an adjustable strap. The face portion 26 on the interior surface 33 is configured to cover an area of the user's face generally bounded by the user's forehead, temples, cheeks, and extends across the nose bridge. Additionally, the face portion 26 is composed of a light-blocking and soft material such as foam. Although a foam material is presently preferred, any soft material or lamination of materials soft and comfortable enough to sleep in may be employed. Other examples of material the sleeping beauty mask 20 can be composed of include nylon, fleece, or silk.

The face portion 26 comprises walls 27 that slightly protrude so as to define laterally symmetrical left and right eye cavities 23. These walls 27 along the perimeter of the eye cavities 23, and in a preferred embodiment, are bounded by another soft material to distinctly mark the eye cavities 23. However, in other embodiments, the eye cavities 23 are just defined with the walls 27, without any additional material that run along the perimeter of the eye cavities 23.

The walls 27 are integral to the face portion 26 and prevent the skin care products from running into the eyes. The eye cavities 23 do not cause the exterior surface of the face portion 26 to protrude. The exterior surface of face portion 26 is smooth through, while the eye cavities 23 appear only on the interior surface.

In addition, the face portion 26 includes internal pockets 21 and 29. These internal pockets 21 and 29, in the preferred embodiment, are on the cheeks and the forehead, respectively. However, other embodiments contain more or less internal pockets 21 and 29. These internal pockets 21 and 29 are made of a semi-permeable material. In some embodiments, the internal pockets 21 and 29 also include porous holes 22.

The internal pockets 21 on the cheeks are laterally symmetrical. In the preferred embodiment, the internal pockets 21 on the cheeks are substantially oval in shape and span the edge of the face portion 26 along the bottom cheek and nose bridge and borders the bottom edge of walls 27 of the eye cavities 23. In other embodiments, the internal pockets 21 on the cheeks are substantially rectangular in shape, if the face portion extends longer and further down on the cheeks of a user.

This internal pocket 29 on the forehead borders the top edge of the face portion 26 and partially extends along the top edges of walls 27 around the eye cavities 23. The internal pocket 29 also is composed of the semi-permeable material, and may include porous holes 22. In some embodiments, the internal pocket 29 may substantially be rectangular as the face portion 26 is enlarged. Other embodiments may have more than one internal pocket 29 on the forehead and may also include internal pockets with the same features on the temples of face portion 26.

Each of the internal pockets 21, 29 includes an opening or an elongated slit 28 that provides access to an interior volume therein. The pockets 21, 29 also include lining around the perimeter of the pocket to act as a barrier and prevent skin care products to seep through to other areas of the sleeping beauty mask 20. In the preferred embodiment, applicator sponge pads can be partially or fully inserted into the interior volume of the pockets 21, 29. It is contemplated that the applicator sponge pads are shaped similarly to the pockets 21, 29 in which it is inserted.

Figure 2:
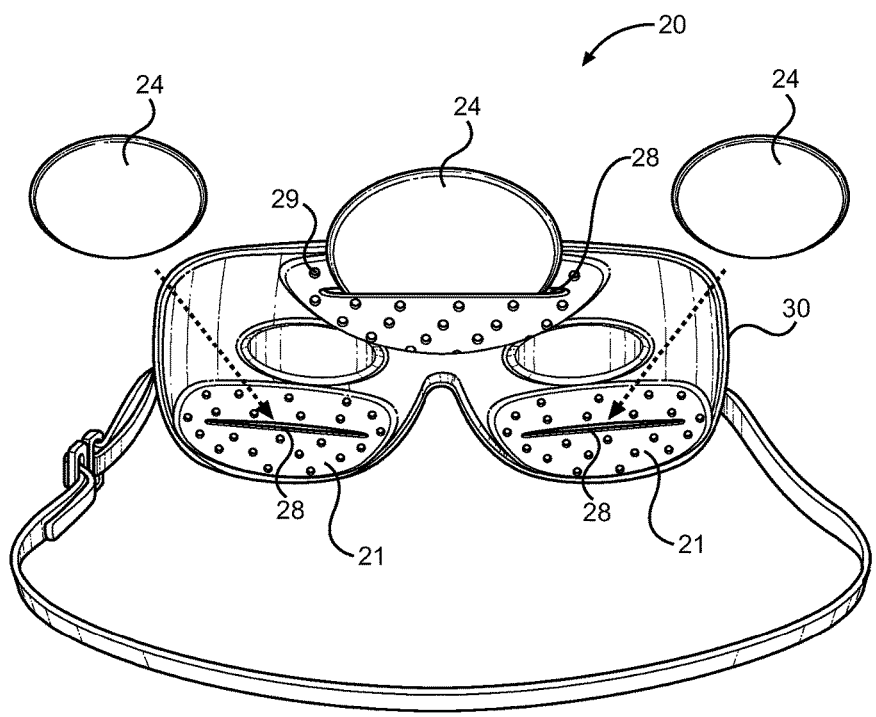
FIG. 2 shows a view of the applicator sponge pads being inserted into the internal pockets of the present invention

Referring to FIG. 2, there is shown a view of the applicator sponge pads 24 being inserted into the slits 28 of the internal pockets 21, 29. In the illustrated embodiment, the pads 24 are partially inserted into the slits 28 of internal pockets 21, 29. Therefore, the skin care product on the exposed portion of the pads 24 can directly contact the skin, while the skin care product on the inserted portion of pads 24 percolate through the semi-permeable material of the pockets 21, 29. In the preferred embodiment, the semi-permeable material is made of rubber. In other embodiments, however, the pockets 21, 29 are made of other permeable material. The interior surface of the face portion 26 is also constructed of a rubber or lined with a similar material, allowing the interior surface to be easily cleaned.

Additionally, the applicator sponge pads are flat so that it does not protrude extensively when inserted in the pockets 21, 29. The applicator sponge pads may be composed of absorbent and soft material that can be impregnated with various types of skin care products such as lotion, serum, or oils. The applicator sponge pads can be partially inserted so that the skin care product that is impregnated on the applicator sponge pads comes in direct contact with the skin. Alternatively, the applicator sponge pads can be fully inserted in the internal pockets 21, 29 so that the skin care product can permeate through the semi-permeable material or porous holes 22 and applied to the user's skin.

The face portion 26 also comprises piping 30 around the peripheral edges of the face portion 26. Any soft material or lamination of materials soft and comfortable enough to sleep in may be employed. The piping 30 may be stitched to the edges of the face portion 26. The piping 30 around the edges ensures no light enters the sleeping beauty mask 20 so that the user may enjoy a natural and effective night of sleep.

Figure 3:
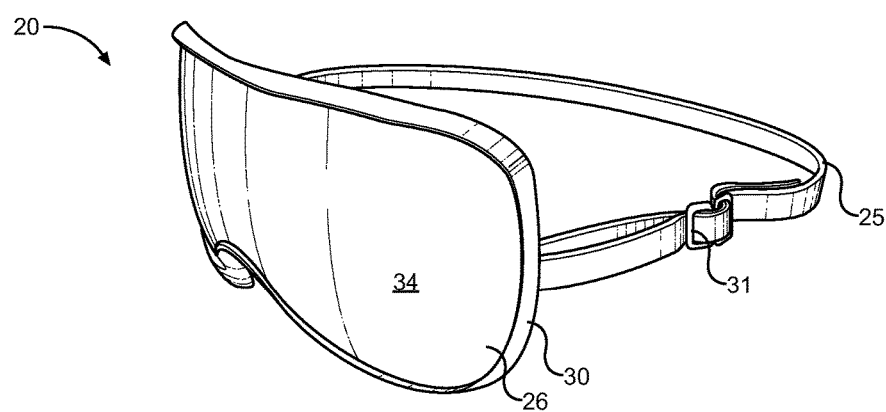
FIG. 3 shows a side perspective of the exterior surface of the present invention.

Referring to FIG. 3, there is shown a side perspective of the exterior surface 34 of the sleeping beauty mask 20. The exterior surface 34 of the face portion 26 is smooth, and does not consist of any of the eye cavities or internal pockets as disposed on the interior surface of the face portion 26. The exterior surface 34 of the face portion 26 is composed of solid fabric or other suitable material that can block out light. Additionally, the piping 30 that is disposed around the face portion 26 can prevent the light from shining through the sides, top, and bottom of the mask. Piping 30 spans the perimeter of the face portion 26 on both the exterior surface and interior surface. Any soft material or lamination of materials soft and comfortable may be employed.

The present invention further comprises an adjustable strap 25 that allows the beauty sleeping mask 20 to be secured around the user's head. The adjustable strap 25 comprises two terminal ends that are affixed to the opposing sides of the face portion 26. In one embodiment, the terminal ends of the adjustable strap 25 may be stitched to the opposing sides of the face portion 26. The adjustable strap 25 can be adjusted in length by means of a buckle 31. The adjustable strap 25 is threaded through the buckle 31 and then folded back onto itself to adjust length of the adjustable strap 25 to comfortably fit an individual's head. Adjustable strap 25 may be composed of a durable silicone material, elastic, or other suitable material that can be stretched and pulled without breaking. In addition, the adjustable strap 25 is an exemplary mechanism to adjust the fit around the user's head; without limitation, other straps such as side release straps or hook and loop fastener disposed on ends of the adjustable strap may be used.

Figure 4:
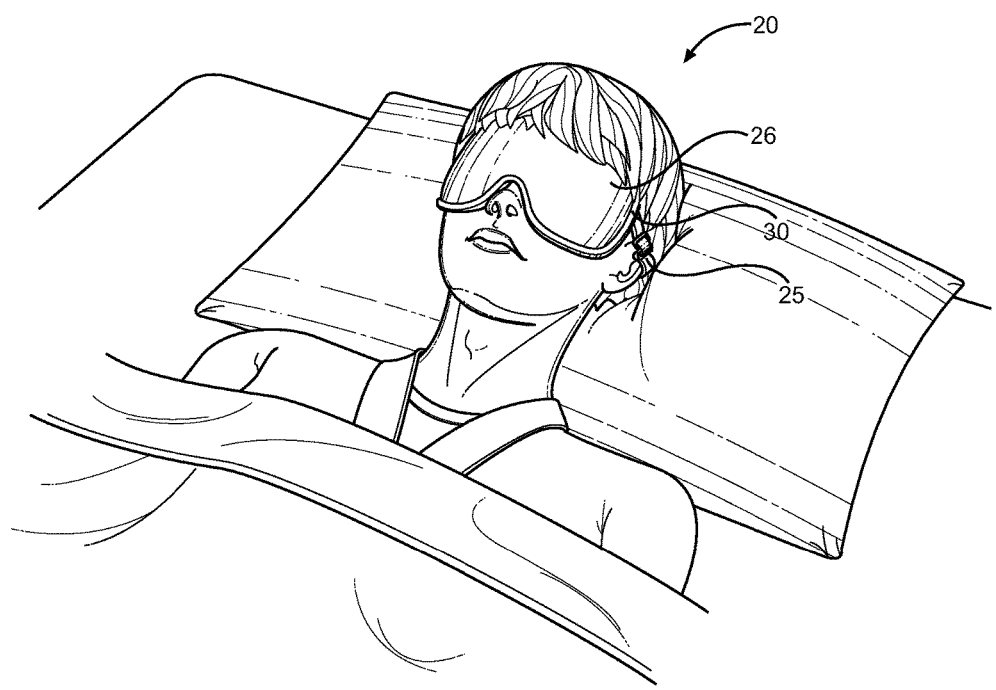
FIG. 4 shows an overhead view of the present invention as used by a person while sleeping.

Referring to FIG. 4, there is an overhead prospective of the sleeping beauty mask 20 in use. The adjustable strap 25 is secured over the head and above the user's ears so that it partially encircles the user's head. The face portion 26 is adapted to cover the user's forehead, eyes, cheeks, and temples, while also extending along the user's nose bridge. The face portion 26 extends along the user's nose in a v-shaped cutout to prevent discomfort around the nose.

The user may impregnate the applicator sponge pads with any desired skin care product, including lotions, serum, oils, and the like. These sponge pads are placed in the internal pockets of the sleeping beauty mask 20. When the user places the sleeping beauty mask on his or her face, and the skin care product can be applied throughout the night. Because the skin care product is disposed on the internal surface of the mask, the skin care products are prevented from being rubbed onto the user's bedding or pillows. Furthermore, the piping 30 is adapted to prevent the skin care products from seeping out of the face portion of the mask.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above descriptions then, it is to be realized that the optimum dimensional relationships for the parts of the invention, to include variations in size, materials, shape, form, function, and manner of operation, assembly and use, are deemed readily apparent and obvious to one skilled in the art, and all equivalent relationships to those illustrated in the drawings and described in the specifications are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A sleeping beauty mask, comprising:
 a face portion comprising an exterior surface that is coextensive with an interior surface, the exterior surface void of any openings;
 a plurality of internal pockets on said interior surface of said face portion;
 an adjustable strap attached to opposing sides of said face portion;
 said face portion adapted to cover a user's forehead, eyes, temples, cheeks, nose bridge;
 a pair of eye cavities disposed on said interior surface of said face portion;
 wherein each of the pair of eye cavities are open along a plane aligned with the interior surface;
 wherein said pair of eye cavities is adapted to be positioned over said user's eyes;
 wherein a wall integral to said interior surface is disposed around a peripheral edge of each of said pair of eye cavities, such that said wall protrudes from said interior surface and is configured to prevent a skin care product disposed on said interior surface from entering said pair of eye cavities;
 wherein said plurality of internal pockets comprises a pocket overlapping a top portion of said wall, such that said pocket is adapted to align with said user's forehead;
 wherein said plurality of internal pockets comprises a pair of laterally symmetrical pockets bordering a bottom edge of the wall of each of said pair of eye cavities, such that said pair of pockets are adapted to align with said user's cheeks;
 wherein each of said plurality of internal pockets further comprises a slit parallel to a top edge of said face portion and disposed on a front surface of an internal pocket between opposing sides thereof, wherein the slit is adapted to provide access to an interior volume of said plurality of internal pockets;
 a lining disposed in each of said plurality of internal pockets adapted to prevent said skin care product from penetrating said exterior surface of said face portion.

2. The sleeping beauty mask of claim 1, wherein said interior volume of said plurality of internal pockets adapted to receive an applicator sponge pad therein.

3. The sleeping mask of claim 1, wherein said plurality of internal pockets is composed of a semi-permeable material.

4. The sleeping beauty mask of claim 1, wherein said adjustable strap comprises a buckle.

5. The sleeping mask of claim 1, further comprising an applicator sponge pad disposed in each of said plurality of internal pockets;
 wherein said applicator sponge pad is adapted to be impregnated with skin care products.

6. The sleeping mask of claim 1, wherein said face portion further comprises a piping along a peripheral edge thereof.

7. The sleeping mask of claim 1, wherein said exterior surface of said face portion is smooth.

8. The sleeping mask of claim 1, wherein said plurality of internal pockets comprises porous holes thereon.

* * * * *